United States Patent [19]

Sarantakis

[11] 3,998,795
[45] Dec. 21, 1976

[54] (ACYL-D-α-AMINO ACID-GLY-GLY-TYR-ALA)[1]-SOMATOSTATIN

[75] Inventor: Dimitrios Sarantakis, West Chester, Pa.

[73] Assignee: American Home Products Corporation, New York, N.Y.

[22] Filed: June 23, 1975

[21] Appl. No.: 589,217

[52] U.S. Cl. ............... 260/78 A; 260/112.5 S; 424/177
[51] Int. Cl.[2] ............ C07C 103/52; A61K 37/00
[58] Field of Search ............ 260/112.5 S, 78 A

[56] References Cited

UNITED STATES PATENTS 3,931,140  1/1976  Sarantakis ............ 260/112.5 S

Primary Examiner—Lewis Gotts
Assistant Examiner—Reginald J. Suyat
Attorney, Agent, or Firm—Richard K. Jackson

[57] ABSTRACT

The growth hormone release inhibiting compound

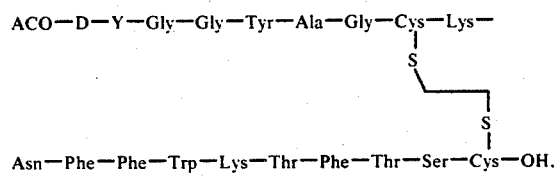

in which Y represents an α-amino acid of the D-series and A is alkyl of 1 to 17 carbon atoms or phenyl; the protamine zinc, protamine aluminum and non-toxic acid addition salts thereof, as well as the corresponding linear octadecapeptide and intermediates therefore are herein described.

10 Claims, No Drawings

(ACYL-D-α-AMINO ACID-GLY-GLY-TYR-ALA)¹-SOMATOSTATIN

BACKGROUND OF THE INVENTION

The structure of the growth hormone release inhibiting factor, somatostatin, had been determined by Brazeau et al., Science, 179, 77(1973). Several techniques for synthesizing somatostatin have been reported in the literature, including the solid phase method of Rivier, J.A.C.S. 96, 2986(1974) and the solution methods of Sarantakis et al., Biochemical Biophysical Research Communications 54, 234(1973) and Immer et al., Helv. Chim. Acta, 57, 730(1974).

DESCRIPTION OF THE INVENTION

In accordance with this invention, there is provided growth hormone release inhibiting compounds of the formula; (ACO-D-Y-Gly-Tyr-Ala) ¹-Somatostatin, in which Y represents an α-amino acid of the D-series and A is alkyl of 1 to 17 carbon atoms or phenyl; the non-cyclic form of the octadecapeptides, the protamine zinc and protamine aluminum adducts and non-toxic acid addition salts thereof as well as the protected intermediates useful for the synthesis of the octadecapeptides. The octadecapeptides of this invention are useful in the treatment of conditions characterized by excessive growth hormone production, such as juvenile diabetes and acromegaly.

The octadecapeptides of this invention ACO-D-Y-Gly-Gly-Tyr-Ala)¹-Somatostatin presents the amino acid sequence;

The octadecapeptide of this invention is prepared by solid phase methodology, employing as the initial reactant the fully protected peptidoresin R-Ala-Gly-Cys (R²)-Lys (R³)-Asn-Phe-Phe-Trp-Lys (R⁴)-Thr(R⁵)-Phe-Thr (R⁶)-Ser (R⁷)-Cys (R⁸)-O-Resin, in which each of the protective R groups are defined, infra. Deprotection of the α-amino protecting group (R) of the alanyl moiety followed by the sequential coupling and deprotection of each of the newly introduced intermediate amino acids tyrosine, glycine, another glycine, followed by the introduction of the terminal D-series amino acid affords the fully protected intermediate R-D-Y-Gly-Gly-Tyr (R¹)-Ala-Gly-Cys (R²)-Lys (R³)-Asn-Phe-Phe-Trp-Lys (R⁴)-Thr (R⁵)-Phe-Thr (R⁶)-Ser (R⁷)-Cys (R⁸)-O-Resin, which, after removal of R, is treated with an excess of an acylating agent to acylate the terminal D-amino acid group. The resulting octadecapeptide resin is totally deprotected and removed from the Resin support by treatment with liquid hydrofluoric acid in the presence of anisole to yield the linear octadecapeptide ACO-D-Y-Gly-Gly-L-Tyr-L-Ala-Gly-L-Cys-L-Lys-L-Asn-L-Phe-L-Phe-L-Trp-L-Lys-L-Thr-L-Phe-L-Thr-L-Ser-L-Cys-OH. If desired, the fully protected octadecapeptide may be removed from the Resin support by methanolysis to yield the 18-Cysteine methyl ester of the fully protected linear octadecapeptide. The methylester may then be converted to the free carboxylic acid by mild hydrolysis and the protecting groups may be subsequently removed by treatment with liquid HF in the presence of anisole or by catalytic (e.g. Pd on BaSO₄) hydrogenation under conditions avoiding attack of the tryptophan moiety.

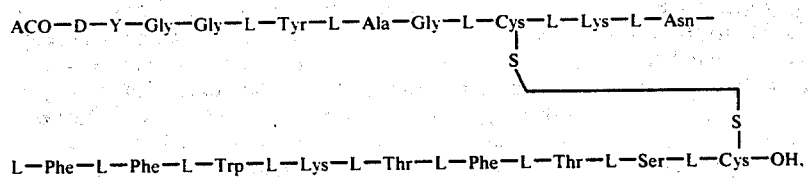

ACO—D—Y—Gly—Gly—L—Tyr—L—Ala—Gly—L—Cys—L—Lys—L—Asn—
                                              |
                                              S
                                              \_____
                                                             |
                                                             S
                                                             |
L—Phe—L—Phe—L—Trp—L—Lys—L—Thr—L—Phe—L—Thr—L—Ser—L—Cys—OH.

in their [7-18]cyclic form and are devoid of the disulfide linkage in the linear form. The protamine zinc and protamine aluminum derivatives of the octadecapeptides represent derivatives conventionally derived from polypeptides for characterization and administrative purposes. The acid addition salts of the octadecapeptides are derived from both inorganic and organic acids known to afford pharmaceutically acceptable non-toxic addition products, such as hydrochloric, hydrobromic, sulfuric, phosphoric, maleic, acetic, citric, benzoic, succinic, malic, ascorbic acid and the like. The acyl group "ACO" is benzoyl or of lower or higher fatty acid derivation containing up to 17 carbon atoms in the alkyl moiety as derived from stearic acid. Although linear alkanoyl groups are greatly preferred because of their availability and lipophilic properties, branched chain alkanoyl groups are acceptable. Of the alkanoyl groups, the lower fatty acyl moieties are preferred, including the acetyl, propionyl, butyryl, pentanoyl, hexanoyl, heptanoyl and octanoyl radicals. The amino acid Y is any α-amino acid of the D-series, terminally situated and selected to provide a terminal amino acid which is compatable with the polypeptide while retarding enzymatic attack to which the amino acid residues of the polypeptide are subject. The preferred α-amino acids of the D-series are D-alanine, D-phenylalanine, D-leucine, D-valine, D-proline and D-α-aminobutyric acid.

The deprotected linear octadecapeptide is readily converted to the [7-18] cyclic disulfide (ACO-D-Y-Gly-Gly-Tyr-Ala)¹-Somatostatin by mild oxidation (e.g. air), preferably through exposure of a solution of the linear compound to atmospheric oxygen. The protamine zinc and protamine aluminum complexes and non-toxic acid addition salts are produced by methods conventional in the polypeptide art.

Thus the intermediates which constitute part of this invention may be represented as:

R-D-Y-Gly-Gly-Tyr (R¹)-Ala-Gly-Cys (R²)-Lys (R³)-Asn-Phe-Phe-Trp-Lys (R⁴)-Thr (R⁵)-Phe-Thr (R⁶)-Ser (R⁷)-Cys (R⁸)-X, in which X represents -OH, OCH₃ or -O-CH₂-[polystyrene resin support];

R represents hydrogen, alkanoyl of 2 to 18 carbon atoms, benzoyl or an α-amino protecting group;

R¹ is a protecting group for the phenolic hydroxyl group of the tyrosyl moiety selected from the group consisting of benzyl, 2,6-dichlorobenzyl, benzyloxycarbonyl and 2-bromobenzyloxycarbonyl;

R² and R⁸ are protecting groups for the sulfhydryl group of the two cysteinyl moiety independently selected from the group consisting of benzyl; methyl, methoxy or nitro-benzyl; trityl, benzyloxycarbonyl, benzhydryl, tetrahydropyranyl, carboxymethyl, acetamidomethyl, benzoyl, benzylthiomethyl, ethylcarbamyl, thioethyl, p-methoxybenzyloxycarbonyl, and the sulfonate salt;

$R^3$ and $R^4$ are members independently selected from the group consisting of hydrogen and a protecting group for the epsilon amino group of the two lysyl moieties selected from benzyloxycarbonyl; halo- or nitro-benzyloxycarbonyl; tosyl, diisopropylmethoxycarbonyl, t-amyloxy-carbonyl and t-butyloxycarbonyl;

$R^5$, $^6$ and $R^7$ are selected from the group consisting of hydrogen and a protecting group for the hydroxyl group of the threonyl and seryl moieties, independently selected from acetyl, benzoyl, terty-butyl, trityl, benzyl, 2,6-dichlorobenzyl, and benzyloxycarbonyl; and Y is an α-amino acid of the D-series.

The α-amino protecting group represented by R may be any group known in the art to be useful in the stepwise synthesis of polypeptides. Illustrative of these known groups for protection of an α-amino group are (a) acyl type protective groups such as formyl, trifluoroacetyl, phthalyl, toluenesulfonyl (tosyl), benzenesulfonyl, nitrophenylsulfenyl, o-nitrophenoxyacetyl, α-chlorobutyryl, and the like; (b) urethan type protecting groups such as benzyloxycarbonyl and substituted benzyloxycarbonyl (p-chlorobenzyloxycarbonyl, p-nitrobenzyloxycarbonyl, p-bromobenzyloxycarbonyl, p-methoxybenzyloxycarbonyl, tert-butyloxycarbonyl, diisopropylmethoxycarbonyl, isopropyloxycarbonyl, allyloxycarbonyl, cyclopentyloxycarbonyl, adamantyloxycarbonyl, cyclohexyloxycarbonyl, phenylthiocarbonyl, and the like; (c) aralkyl type protecting groups as illustrated by triphenylmethyl, benzyl, and the like; and (d) trialkylsilane groups such as trimethyl silane. The preferred α-amino protecting groups defined by R and employed with each amino acid introduced into the polypeptide is tert-butyloxycarbonyl.

The criterion for selecting protecting groups for $R^{1-8}$ are (a) the protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis of the desired amino acid sequence, under reaction conditions that will not alter the peptide chain.

The group $-O-CH_2-$[polystyrene resin support] defining X in the intermediates of this invention described supra, represents the ester moiety of one of the many functional groups of the polystyrene resin support.

The solid phase method of preparing the octadecapeptide of this invention is generally known in the art and is described by Merrifield, J.A.C.S., 85, 2149(1963). The general sequence followed was quite similar to that of Rivier, J.A.C.S. 96, 2986 (1974), although α-tert-butyloxycarbonyl-ε-2-chlorobenzyloxycarbonyl-L-lysine was employed as a less labile reactant during deprotection of the α-amino group than the ε-benzyloxycarbonyl group of the reference. The resin support employed may be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky et al., Chem. Ind. (London) 38, 1597–98 (1966). A chloromethylated resin is commercially available from Bio Rad Laboratories Richmand, California and the preparation of such a resin is described by Steward et al., "Solid Phase Peptide Synthesis" (Freeman & Co., San Francisco 1969), Chapter 1, pp 1–6. The α-amino and sulfhydryl protected cysteine is coupled to the chloromethylated resin according to the procedure of Gisin, Helv. Chim. Acta., 56, 1476(1973). Following the coupling of the α-amino and sulfhydryl protected cysteine to the resin support, the α-amino protecting group is removed by standard methods employing trifluoroacetic acid in methylene chloride, trifluoroacetic acid alone or HCl in dioxane. The deprotection is carried out at a temperature between about 0° C. and room temperature. After removal of the α-amino protecting group the remaining α-amino protected amino acids are coupled, seriatim, in the desired order to obtain the product. Alternatively, multiple amino acid groups may be coupled by the solution method prior to coupling with the resin supported amino acid sequence. The selection of an appropriate coupling reagent is within the skill of the art. A particularly suitable coupling reagent is $N,N^1$-diisopropyl carbodiimide. Other applicable coupling agents are (1) carbodiimides (e.g. $N,N^1$-dicyclohexycarbodiimide, N-ethyl $N^1$-(α-dimethylamino propyl carbodiimide); (2) cyanamides (e.g. N,N-dibenzylcyanamide; (3) ketenimines; (4) isoxazolium salts (e.g. n-ethyl-5-phenyl isoxazolium-3'-sulfonate; (5) monocyclic nitrogen containing heterocyclic amides of aromatic character containing one through four nitrogens in the ring such as imidazolides, pyrazolides, 1,2,4-triazolides, specific heterocyclic amides that are useful include N,N-carbonyl diimidazole, N,N'-carbonyl-di-1,2,4-triazole; (6) alkoxylated acetylene (e.g. ethoxyacetylene); (7) reagents which form a mixed anhydride with the carboxyl moiety of the amino acid (e.g. ethylchloroformate, isobutylchloroformate) and (8) nitrogen containing heterocyclic compounds having a hydroxy group on one ring nitrogen (e.g. N-hydroxyphthalimide, N-hydroxysuccinimide, 1-hydroxybenzotriazole). Other activating reagents and their use in peptide coupling are described by Schroder & Lubke supra, in Chapter III and by Kapoor, J. Pharm. Sci., 59, pp. 1–27, (1970).

Each protected amino acid or amino acid sequence is introduced into the solid phase reactor in about a fourfold excess and the coupling is carried out in a medium of dimethylformamide: methylene chloride (1:1) or in dimethylformamide or methylene chloride alone. In cases where incomplete coupling occurs the coupling procedure is repeated before removal of the α-amino protecting group, prior to introduction of the next amino acid to the solid phase reactor. The success of the coupling reaction at each stage of the synthesis is monitored by the ninhydrin reaction as described by E. Kaiser et al., Analyt. Biochem, 34, 595 (1970).

The in vivo activity of the octadecapeptides of this invention was established with $(CH_3CO-D-Ala-Gly-Gly-L-Tyr-L-Ala)^1$-Somatostatin as a representative member of the octadecapeptides of this invention by injecting Nembutal intraperitoneally into rats weighing between 200 and 250 grams in an amount of 50 milligrams per kilogram body weight. After five minutes, the octadecapeptide was administered to the rats, subcutaneously, at a dose of 1000 micrograms per kilogram body weight. The rats blood was sampled 15 minutes after administration of the octadecapeptide and the amount of growth hormone present in the plasma was determined by radioimmunoassay. The octadecapeptide afforded a blood plasma concentration of growth hormone in the test animals of 74 ± 16 nanograms per milliliter as opposed to the concentration of growth hormone in the control animals of 236 ± 30 nanograms per milliliter, at a statistical certainty of p<0.01.

The activity of the octadecapeptides of this invention is surprising in that the peptide contains more amino acid residues than somatostatin itself and still exhibits inhibition of growth hormone secretion in terms of a reduction of growth hormone concentration in blood plasma. Like somatostatin, the octadecapeptides of this invention are useful in the prevention of excessive secretion of growth hormone in domestic animals and the human. From the know relationship between growth hormone control in standard experimental animals and the human, the activity of the disclosed octadecapeptides characterizes them as useful in the treatment of acromegaly and juvenile diabetes in the same manner as somatostatin itself. Administration of the octadecapeptides of this invention may be by conventional routes common to somatostatin and related polypeptides, under the guidance of a physician, orally or parenterally, in an amount dictated by the extent of the dysfunction as determined by the physician. The compounds may be administered alone or in conjunction with conventional pharmaceutically acceptable carriers and adjuvants, in unit dosage form containing from about 0.2 to about 100 milligrams per kilogram host body weight. Furthermore, the protamine zinc or protamine aluminum adducts present desireable administrable forms of the octadecapeptides as is conventional in therapy involving the use of polypeptides.

In the following preparatory scheme, the abbreviations employed are:
Boc = tertiary butyloxycarbonyl
MBzl = p-methoxybenzyl
ClZ = 2-chlorobenzyloxycarbonyl
Bzl = benzyl
Cl$_2$Bzl = 2,6-dichlorobenzyl.

EXAMPLE I

N-α-acetyl-D-alanyl-glycyl-glycyl-O-2,6-dichlorobenzyl-L-tyrosyl-L-alanyl-glycyl-S-p-methoxybenzyl-L-cysteinyl-N-ε-2-chlorobenzyloxycarbonyl-L-lysyl-L-asparaginyl-L-phenylalanyl-L-phenylalanyl-L-tryptophyl-N-ε-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl-hydroxymethyl polystyrene The peptido resin Boc-Ala-Gly-cys(SMBzl)-Lys(ClZ)-Asn-Phe-Phe-Trp-Lys(ClZ)-Thr(Bzl)-Phe-Thr(Bz)-Ser(Bzl)-cys(SMBzl)-O-Resin(8 g.) was prepared by conventional solid phase techniques reported in the literature. Deprotection of the α-amino group of alanine was effected by treatment with trifluoroacetic acid CH$_2$Cl$_3$ - 1,4-dithioerythritol (1:1:0.5%) for 30 minutes at room temperature in an Automatic Peptide Synthesizer, Beckman 990. The peptido resin was washed with CH$_2$Cl$_2$ × 3, dimethylformamide × 1, dimethylformamide-triethylamine 12%, CH$_2$Cl$_2$ — triethylamine 12% CH$_2$Cl$_2$ × 3. Ninhydrin test according to Kaiser et al., Anal. Biochem. 34, 595 (1970) was positive. The peptido resin was treated with Boc-Tyr-(Cl$_2$Bzl)-OH (11 g.) in dimethylformamide CH$_2$Cl$_2$ (2:1) followed by diisopropylcarbodiimide (30 ml. 1M-solution in CH$_2$Cl$_2$) in two portions. The mixture was stirred for 4 hours then filtered and washed with CH$_2$Cl$_2$ × 3, dimethylformamide × 3, CH$_2$Cl$_2$ × 3 and the cycle was repeated for the incorporation of Boc-Gly-OH, Boc-Gly-OH, Boc-D-Ala-OH and finally the deprotected peptido resin was treated with a large excess of acetic anhydride to obtain the title material. Yield 12 g.

Amino acid analysis, Asp (1) 1, Gly (3) 3, Lys (2) 1.83, Thr (2) 0.95, Ser (1) 0.10, Ala (2) 2.1, Tyr (1) 0.83, Phe (3) 3.16, Cys, Trp, not determined.

EXAMPLE II

N-α-Acetyl-D-alanyl-glycyl-glycyl-L-tyrosyl-L-alanyl-glycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine (7–18 disulfide) diacetate The peptido resin of the previous example (7 g.) was mixed with anisole (8 ml.) and treated with liquid HF (150 ml.) at 0° C. for 60 minutes then the excess HF was removed as fast as possible in vacuo ( ca. 1 hour) and the residue was extracted with 2M-acetic acid (ca. 150 ml.). The resin was removed by filtration and the filtrate was lyophilized, then the lyophilizate was suspended in 2 lt. 0.1 M-aqueous ammonium acetate and oxidized by air for 24 hours and at pH 7.8. The mixture was acidified with glacial acetic acid to pH 6.5 and then lyophilized to give a white solid. This solid was taken in a small volume of 1 M-acetic acid and passed through a column (2.5 I.D. × 150 cm.) packed with swollen Sephadex G-15. Fractions of 6 ml. each were collected and the compound was located by the Folin-Lowry color test. The fractions in tubes 49 to 157 were pooled and lyophilized to aford 834 mg. of a fluffy solid.

R$_f$ (n-butanol-water-acetic acid-pyridine, 30:24;6:20) 0.85 with a trace of impurity at 0.55.

Amino acid analysis: Asp (1) 0.88, Thr (2) 1.87, Ser (1) 0.95, Gly (3) 3.41, Ala (2) 2.56, Tyr (1) 0.89, Phe (3) 2.88, Lys (2) 2, Cys and Trp not determined.

Acetic anhydride, as employed in the preceding examples, is illustrative of one type of acylating agent. As is readily recognized by the art skilled, other techniques for introducing the acyl group ACO as the α-amino substituent of the D-amino acid, such as via mixed anhydrides, acylhalides, etc., are applicable. The reaction sequence illustrated above, is modified simple for the production of each of the polypeptides of this invention by substituting the desired α-amino acid group of the D-series for D-Ala (illustrated), and preferably one of D-alanine, D-phenylalanine, D-leucine, D-valine, D-proline or D-α-amino butyric acid, and by selection and introduction of the terminal acyl group to provide the desired degree of lipophilicity to aid absorption of the polypeptide in the body.

What is claimed is:
1. A compound selected from the group consisting of

ACO-D-Y-Gly-Gly-L-Tyr-L-Ala-Gly-L-Cys-L-Lys-L-Asn-
                                                                  S
                                                                  |
                                                                                                                                                                                                 S
L-Phe-L-Phe-L-Trp-L-Lys-L-Thr-L-Phe-L-Thr-L-Ser-L-Cys-OH,

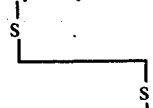

the corresponding linear octadecapeptide, the protamine zinc, protamine aluminum and non-toxic acid addition salts thereof, in which A is alkyl of 1 to 17 carbon atoms or phenyl and Y is an α-amino acid of the D-series.

2. The octadecapeptide of claim 1 in which A is methyl, ethyl, propyl, butyl, pentyl, hexyl or heptyl.

3. The octadecapeptide of claim 1 in which Y is D-alanine, D-phenylalanine, D-leucine, D-valine, D-proline or D-α-amino butyric acid.

4. A compound selected from the group consisting of

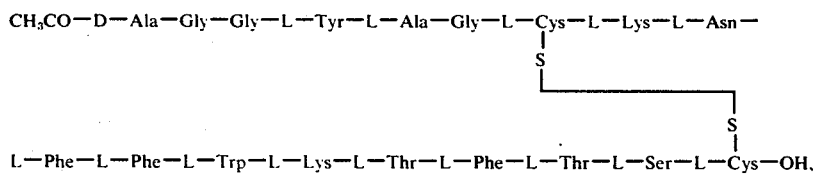

the corresponding linear octadecapeptide, the protamine zinc, protamine aluminum and non-toxic acid addition salts thereof.

5. The octadecapeptide of claim 4 which is CH$_3$CO-D-alanylglycyl-glycyl-L-tyrosyl-L-alanylglycyl-L-cysteinyl-L-lysyl-L-asparaginyl-L-phenylalanyl-L-phenylalanyl-L-tryptophy-L-lysyl-L-threonyl-L-phenylalanyl-L-threonyl-L-seryl-L-cysteine.

6. The octadecapeptide of claim 4 which is CH$_3$CO-D-alanylglycyl-glycyl-L-tyrosyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine [7–8 disulfide].

7. An octadecapeptide of the formula R-D-Y-Gly-Gly-Tyr-(R$^1$)-Ala-Gly-Cys(R$^2$)-Lys(R$^3$)-Asn-Phe-Phe-Trp-Lys(R$^4$)-Thr (R$^5$)-Phe-Thr (R$^6$)-Ser (R$^7$)-Cys (R$^8$)-O-X in which R is a member selected from the group consisting of hydrogen, alkanoyl of 2 to 18 carbon atoms, benzoyl, and an α-amino protecting group;

R$^1$ is a protecting group for the phenolic hydroxyl group of the tyrosyl moiety selected from the group consisting of benzyl, 2,6-dichlorobenzyl, benzyloxycarbonyl and 2-bromobenzyloxycarbonyl;

R$^2$ and R$^8$ are protecting groups for the sulfhydryl group of the two cysteinyl moiety independently selected from the group consisting of benzyl; methyl, methoxy or nitro-benzyl; trityl, benzyloxycarbonyl, benzhydryl, tetrahydropyranyl, carboxymethyl, acetamidomethyl, benzoyl, benzylthiomethyl, ethylcarbamyl, thioethyl, p-methoxybenzyloxycarbonyl, and the sulfonate salt;

R$^3$ and R$^4$ are members independently selected from the group consisting of hydrogen and a protecting group for the epsilon amino group of the two lysyl moieties selected from benzyloxycarbonyl; halo- or nitro-benzyloxycarbonyl; tosyl, diisopropylmethoxycarbonyl, t-amyloxy-carbonyl and t-butyloxycarbonyl;

R$^5$, R$^6$ and R$^7$ are selected from the group consisting of hydrogen and a protecting group for the hydroxyl group of the threonyl and seryl moieties, independently selected from acetyl, benzoyl, tert-butyl, trityl, benzyl, 2,6-dichlorobenzyl, and benzyloxycarbonyl;

X is a member selected from the group consisting of hydroxy, methoxy and -O-CH$_2$-[polystyrene resin support], wherein said polystyrene resin is cross linked with from 0.5 to about 3 percent divinylbenzene; and Y is an α-amino acid of the D-series.

8. A compound of claim 7 in which Y is selected from the group consisting of D-alanine, D-phenylalanine, D-leucine, D-valine, D-proline and D-α-aminobutyric acid.

9. A compound of claim 7 in which Y is D-alanine, R is t-butyloxycarbonyl, R$^1$ is 2,6-dichlorobenzyl, R$^2$ and R$^8$ are p-methoxybenzyl, R$^3$ and R$^4$ are 2-chlorobenzyloxycarbonyl and R$^5$ and R$^6$ and R$^7$ are benzyl.

10. The compound of claim 7 in which Y is D-alanine, R is acetyl, R$^1$ is 2,6-dichlorobenzyl, R$^2$ and R$^8$ are p-methoxybenzyl, R$^3$ and R$^4$ are 2-chlorobenzyloxycarbonyl and R$^5$ and R$^6$ and R$^7$ are benzyl.

* * * * *